United States Patent

Martin et al.

[11] 4,187,298
[45] Feb. 5, 1980

[54] 2'N-ACYL AND ALKYL FORTIMICIN B AND DERIVATIVES, 4,2'-N,N'DIACYL AND DIALKYL FORTIMICIN B DERIVATIVES 4-N-ACYL-2'-N-ALKYL AND 4-N-ALKYL-2'-N-ACYL FORTIMICIN B DERIVATIVES

[75] Inventors: Jerry R. Martin; John S. Tadanier, both of Waukegan; Paulette Collum, Zion, all of Ill.

[73] Assignee: Abbott Laboratories, North Chicago, Ill.

[21] Appl. No.: 863,012

[22] Filed: Dec. 21, 1977
(Under 37 CFR 1.47)

[51] Int. Cl.² ................. A61K 31/71; C07H 15/22
[52] U.S. Cl. ........................ 424/180; 536/4; 536/17 R
[58] Field of Search ............ 536/17; 260/345.9 R; 424/118, 180

[56] References Cited

U.S. PATENT DOCUMENTS

| 3,925,353 | 12/1975 | Umezawa et al. | 536/17 |
| 3,931,400 | 1/1976 | Nara et al. | 424/118 |
| 3,976,768 | 8/1976 | Nara et al. | 424/118 |
| 3,985,727 | 10/1976 | Daniels | 536/17 |

Primary Examiner—Johnnie R. Brown
Attorney, Agent, or Firm—Robert L. Niblack; Gildo E. Fato; Joyce R. Niblack

[57] ABSTRACT

2'-N-Acyl and alkyl fortimicin B and fortimicin B derivatives, 4,2'-N,N'-diacyl and dialkyl derivatives, 4-N-acyl-2'-N-alkyl and 4-N-alkyl-2'-N-acyl fortimicin B derivatives represented by the formula

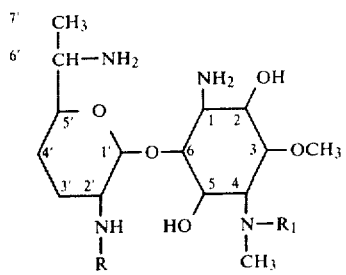

wherein: R is acyl, aminoacyl, N-monoloweralkylaminoacyl, N,N-diloweralkylaminoacyl, hydroxy-substituted aminoacyl, hydroxyacyl, an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl or N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, an amino acid residue, hydroxyacyl, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen and the pharmaceutically acceptable salts thereof; pharmaceutical compositions containing the compounds; and methods of making and using the compounds. The compounds are useful as antibiotics, intermediates, and are further useful in making moth proofing agents and pickling inhibitors.

21 Claims, No Drawings

2′-N-ACYL AND ALKYL FORTIMICIN B AND DERIVATIVES, 4,2′-N,N′DIACYL AND DIALKYL FORTIMICIN B DERIVATIVES 4-N-ACYL-2′-N-ALKYL AND 4-N-ALKYL-2′-N-ACYL FORTIMICIN B DERIVATIVES

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin group of aminoglycoside antibiotics provide compounds which are less toxic than the parent antibiotic. Further, in the same family series mentioned above, certain modifications alter the antibacterial spectrum advantageously either by increasing the intrinsic activity or increasing activity against resistant strains.

Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic. It is known that in the naturally occuring fortimicin aminoglycoside antibiotics blocking the 2-hydroxy group inactivates the antibiotic.

The present invention provides new and useful fortimicin derivatives.

SUMMARY OF THE DISCLOSURE

2′-N-acyl and alkyl fortimicin B and derivatives, 4,2′-N,N′-diacyl and dialkyl fortimicin B derivatives, 4-N-acyl-2′-N-alkyl and 4-N-alkyl-2′-N-acyl fortimicin B derivatives are provided by this invention as well as their salts, intermediates, processes for making the compounds, and compositions and methods employing the compounds.

The fortimicin derivatives of this invention are antibiotics which are effective against various Gram-negative and Gram-positive bacteria and can be administered orally or parenterally in daily dosages of from about 1 to about 100 mg/kg of body weight daily to mammalian patients showing symptoms of infection caused by one of the susceptible bacteria.

The compounds can also be used as preservatives for various industrial solutions, in antibacterial scrub solutions for cleaning laboratory bench tops and the like. They are also useful as intermediates in preparing other fortimicin B derivatives which have anti-bacterial activity.

The base fortimicin derivatives of this invention are amines and form salts with fluosilicic acid which are useful as mothproofing agents according to the teachings of U.S. Pat. Nos. 1,915,334 and 2,075,359. They also form salts with thiocyanic acid which condense with formaldehyde to form resinous materials useful as pickling inhibitors as taught in U.S. Pat. Nos. 2,425,320 and 2,606,155.

Derivatives useful in the preparation of the compounds of this invention are provided as well as method of making and using the compounds and compositions employing the compounds.

DETAILED DESCRIPTION OF PREFERRED EMBODIMENTS

The present invention provides 2′-N-acyl and alkyl fortimicin B and derivatives, 4,2′-N,N′-diacyl and dialkyl derivatives, 4-N-alkyl-2-N acyl and 4-N-acyl-2′-N-alkyl fortimicin B derivatives represented by Formula I:

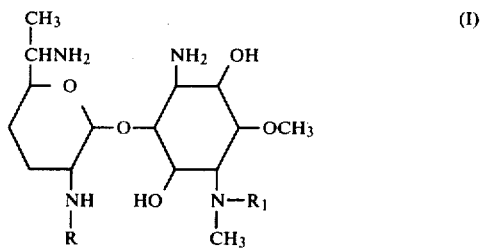

wherein R is acyl, aminoacyl, N-monoloweralkylaminoacyl, hydroxyacyl, N,N-diloweralkylaminoacyl, hydroxy-substituted aminoacyl, an amino acid residue, loweralkyl, aminoloweralkyl, hydroxyloweralkyl, aminohydroxyloweralkyl, N-loweralkylaminoloweralkyl, N,N-diloweralkylaminoloweralkyl, hydroxyloweralkyl, N-loweralkylaminohydroxyloweralkyl or N,N-diloweralkylaminohydroxyloweralkyl and $R_1$ is acyl, aminoacyl, N-monoloweralkylaminoacyl, N,N-diloweralkylaminoacyl, hydroxy-substituted aminoacyl, hydroxyacyl an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, and the pharmaceutically acceptable salts thereof.

The term "pharmaceutically acceptable salts" refers to non-toxic acid addition salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The term "acyl" refers to groups represented by the formula

wherein $R_1$ is loweralkyl, i.e., acetyl, propionyl, butyryl, etc.

"Lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

All amino acid residues are in the D, L or DL configuration unless otherwise specified and include, but are not limited to glycyl, alanyl, sarcosyl, tyrosyl, phenylalanyl, methionyl, seryl, lysyl, asparaginyl, isoleucyl, leucyl, histidyl, threonyl, aspartyl, asparaginyl, valyl, prolyl, glutaminyl, tryptophanyl, glutamyl and the like.

The 2'-N-acylfortimicin B derivatives of Formula I can be prepared by rearrangement of the corresponding 4-N-substituted fortimicins B of Formula II

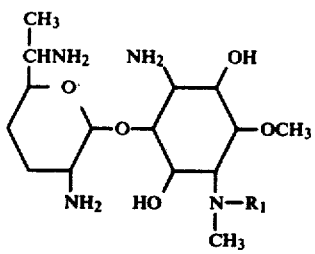

(II)

wherein R₁ is as defined in Formula I, including fortimicin A, represented by Formula III

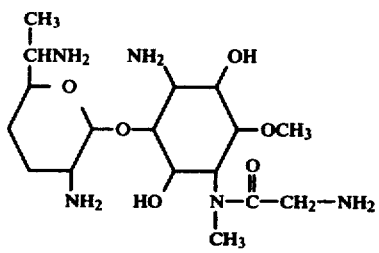

(III)

Fortimicin A and fortimicin B are prepared according to the method of U.S. Pat. Nos. 3,976,768 and 3,931,400, respectively. The preparation of representative 4-N-acyl fortimicin B derivatives is set forth in the examples herein.

The intermediates of this invention are represented by Formula IV:

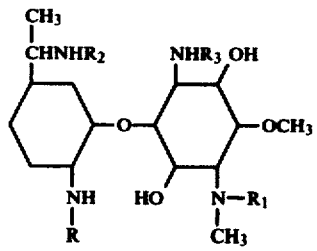

(IV)

wherein R is as defined in Formula I or RZ wherein Z is benzyloxycarbonyl, R₁ is as defined in Formula I or RZ wherein Z is benzyloxycarbonyl, R₂ is hydrogen or benzyloxycarbonyl and R₃ is hydrogen or benzyloxycarbonyl with the limitation that R₁, R₂ and R₃ cannot each be hydrogen.

The 2'-N-acetyl, 2'-N-glycyl, and the like 2'-N-acyl or substituted acyl fortimicins B can readily be prepared by rearrangement of corresponding 4-N-substituted fortimicins. In one method of preparation, the stable acid addition salts of the 4-N-substituted fortimicins are converted to the free bases by, for example, use of a suitable anion exchange resin. The 2'-N-substituted fortimicins B are then prepared by placing the unstable 4-N-substituted fortimicin free bases in water solution which readily rearranges the C₄-methylamino substituent to give the corresponding 2'-N-substituted fortimicins B. Treatment of the 2'-N-substituted fortimicins B with suitable N-actylating agents such as N-(benzyloxycarbonyl)oxysuccinimide in a solvent system such as N-N-dimethylformamide or methanol-water results in an 1,2',6' N-protected intermediate, with a free C₄-methylamino group which can be acylated with a variety of activated carboxylic acid derivatives, such as carboxylic acid anhydride, a carboxylic acid chloride, an active carboxylic acid ester, or a carboxylic acid azide.

The active esters may be conveniently prepared by reacting the appropriate carboxylic acid,

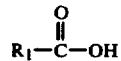

with, for example, 1-hydroxybenzotriazole, N-hydroxysuccinimide, or N-hydroxy-5-norborene-2,3-dicarboximide according to the method of M. Fujino et al., Chem Pharm. Bull, Japan, 22 1857 (1974) wherein R₁ is an acyl group as defined in Formula I.

After completion of the N-acylation of the C₄-N-methylamino group, it is necessary to remove the benzyloxycarboxyl protecting groups, which can conveniently be carried out by hydrogenolysis over a palladium on carbon catalyst. The fortimicin analogs thus prepared are conveniently isolated as the hydrochloride salts (or other acid addition salts) when the hydrogenolysis is carried out in the presence of a slight excess of hydrochloric acid or another suitable acid.

The 2'-N-alkylfortimicins B are conveniently prepared by treatment of the 2'-N-acylfortimicins B with a suitable reducing agent such as a hydride of diborane or a metal hydride such as lithium aluminum hydride. The resulting 2'-N-alkylfortimicins B derivative can then be treated with a suitable N-acy- scribed above. Deprotection is then completed by hydrogenolysis in the presence of 5% palladium on carbon catalyst which results in the desired 2'-alkyl or 2'-acyl derivatives.

The 4,2'-di-N-alkylfortimicins B are conveniently prepared by treating the desired N-protected 4,2'-di-N-acylfortimicin B with a suitable reducing agent, e.g., the hydride of diborane. Deblocking by hydrogenolysis as described above gives 2'-N-alkyl-4-N-alkylfortimicins B. Alternatively, the 4,2'-di-N-alkylfortimicins can be prepared by reduction of a suitable 4'-N-acyl-2'-N-alkylfortimicin B. For example, a 4-N-acyl-2'-N-alkyl fortimicin B or an N-protected 4-N-acyl-2'-N-alkylfortimicin B may be treated with a suitable reducing agent, e.g., the hydride of diborane. In the case of the resulting N-protected 4,2-di-N-alkylfortimicins B, the N-blocking groups can be conveniently removed by hydrogenolysis providing the 4,2'-di-N-alkylfortimicin B.

Alternatively, the 2'-N-acyl derivatives of this invention can be prepared by reacting fortimicin B with tert-butyl-S-(4,6-dimethyl-pyrimidin-2-yl)thiolcarbonate to obtain the 2'-tert-butyloxycarbonyl (Boc) fortimicin B intermediate.

The 2'-Boc-intermediate is then reacted with a suitable acylating agent, i.e., N-(benzyloxycarbonyloxy)-succinimide which results in the 1,6'-di-N-benzyloxycarbonyl-2'-Boc-fortimicin B intermediate. Treatment of the latter intermediate with an active ester of N-protected glycine, e.g., the hydrosuccinimide ester of N-benzyloxycarbonylglycine in the presence of a suitable solvent system such as N,N-dimethylformamide-methanol-water results in the 2'-Boc-tri-N-benzyloxycarbonylfortimicin B intermediate.

2-N-Alkylation or acylation is then conveniently accomplished by reacting the 2'-deprotected intermediate with a suitable aldehyde (R₁CHO) in the presence of sodium borohydride or by treatment with a carboxylic acid ester as desodium sodium borohydride. Deprotection is then completed by hydrogenolysis in the presence of 5% palladium on carbon catalyst which results in the desired 2'-alkyl or 2'-acyl derivatives.

The following examples further illustrate the present invention. Numbers in parentheses refer to the compound number in the reaction scheme of Table 1.

EXAMPLE 1

2'-N-Glycylfortimicin B (2)

An aqueous solution of 10.0 g of fortimicin A disulfate (1) is passed through a column of an anion exchange resin, quaternary ammonium styrene type, e.g., Bio-Rad Laboratories, AG®2-×8 resin, 100–200 mesh, (hydroxyl form), sufficient to remove the sulfate ion. The basic elutes are collected and diluted with water to a 1% solution based on starting fortimicin A disulfate. After standing at 37° C. for 20 days the water is evaporated under reduced pressure to leave an oil. A 2.07 g portion of the oil is chromatographed on a column (2.2×52 cm) of a cation exchange resin, carboxylic type, e.g., Bio-Rad Laboratories, Bio-Rex 70, 100–200 mesh, (ammonium form) and eluted with 0.1 N ammonium hydroxide. Elutes containing only 2'-N-glycylfortimicin B are collected, evaporated to a small volume under reduced pressure and lyophilized to give 1.349 g of white solid: $[\alpha]_D^{25}+41.6°$ (c 1.09, $CH_3OH$); IR 3370, 1660 and 1540 cm$^{-1}$; NMR ($D_2O$) $\delta 1.52$ ($C_{6'}$—$CH_3$, J=7.0 Hz), 2.85 ($C_4$—$NCH_3$), 3.75 (CO—$CH_2$—N—), 3.93 ($OCH_3$), 5.60 ($H_{1'}$, J=4.0 Hz).

Anal. Calcd. for $C_{17}H_{35}N_5O_6$: C, 50.36; H, 8.70; N, 17.27. Found: C, 49.07; H, 8.70; N, 17.30.

EXAMPLE 2

2'-N-(N-Benzyloxycarbonylglycyl)-1,6'-di-N-benzyloxycarbonylfortimicin B (3)

A stirred solution of 0.333 g of 2'-N-glycylfortimicin B in 4.5 ml of water and 9.0 ml of methanol, cooled to 4° C. in an ice bath, is treated with 0.666 g of N-(benzyloxycarbonyloxy)succinimide. Stirring is continued at 4° C. for 3 hours and then at room temperature for 20 hours. The resulting solution is concentrated under reduced pressure to an oil. The oil is shaken with a mixture of 150 ml of chloroform and 75 ml of water. The chloroform layer is separated and washed with 75 ml of water. The aqueous portions are washed in series with two 75 ml portions of chloroform. The chloroform solutions are combined and dried over anhydrous magnesium sulfate. Evaporation of the chloroform under reduced pressure leaves 0.596 g of product. The product is chromatographed on a column (1.8×48 cm) of silica gel prepared and eluted with a solvent system consisting of chloroform methanol-concentrated amonium hydroxide (23.4:1.4:0.1 v/v/v) to yield 0.254 g of 2'-N-(N-benzyloxycarbonylglycyl-1,6'-di-N-benzyloxycarbonylfortimicin B: $[\alpha]_D^{23}+15.8°$ (c 1.04, $CH_3OH$); IR 3410, 3330, 1705 and 1515 cm$^{-1}$;

EXAMPLE 3

Tetra-N-benzyloxycarbonyl-2'-N-glycylfortimicin A (4)

To a stirred solution of 0.234 g of 2'-N-(N-benzyloxycarbonylglycyl)-1,6'-di-N-benzyloxycarbonylfortimicin B and 0.939 g of 1-hydroxybenzotriazole monohydrate in 2.0 ml tetrahydrofuran is added 0.087 g of N,N-dicyclohexylcarbodiimide in 2.0 ml of tetrahydrofuran. Stirring is continued for 20 hours at room temperature. Insoluble dicyclohexylurea is removed by filtration and the filtrate is concentrated to dryness under reduced pressure to give 0.408 g of lemon-yellow solid. The solid is chromatographed on a column (1.8×42 cm) of silica gel eluted with a solvent system consisting of benzenemethanol-95% ethanol-concentrated ammonium hydroxide (23.5:1.4:2.0:0.2 v/v/v/v) to give 0.235 g of tetra-N-benzyloxycarbonyl-2'-N-glycylfortimicin A: $[\alpha]_D^{24}+48.9$ (c 1.0, $CH_3OH$); IR 3410, 3350, 1703, 1636 and 1497 cm$^{-1}$; NMR ($CDCl_3$) $\delta 1.05$ ($C_{6'}$—$CH_3$, J=7.0 Hz), 2.93 ($C_4$—$NCH_3$), 3.29 ($OCH_3$), 5.02 (Cbz—$CH_2$), 7.27 (Cbz. Aromatic)

Anal. Calcd. for $C_{51}H_{62}N_6O_{15}$: C, 61.31; H, 6.26; N, 8.41. Found: C, 61.28; H, 6.42; N, 8.30.

EXAMPLE 4

2'-N-Glycylfortimicin A tetrahydrochloride (5)

A solution of 0.235 g of tetra-N-benzyloxycarbonyl-2'-N-glycylfortimicin A in 40 ml of 0.2 N hydrochloric acid in methanol in hydrogenolyzed for 4 hours under 3 atmospheres of hydrogen in the presence of 0.235 g of 5% palladium on carbon. The catalyst is removed by filtration through a celite mat. The filtrate is concentrated to dryness and excess hydrochloric acid is removed by repeated co-distillation with methanol under reduced pressure to give 0.153 g of 2'-N-glycylfortimicin A tetrahydrochloride: $[\alpha]_D^{25}+84.6°$ (c 1.0, $CH_3OH$); IR 1640, 1620, 1563 and 1480 cm$^{-1}$; NMR ($D_2O$) $\delta 1.80$ ($C_{6'}$—$CH_3$, J=7.0 Hz), 3.58 ($C_4$—$NCH_3$), 3.94 ($OCH_3$), 5.54 ($H_{1'}$, J=3.0). Mass spec. M$^+$ Calcd. 444.2696, Measured 444.2699.

EXAMPLE 5

1,2',6'-Tri-N-benzyloxycarbonylfortimicin B (7)

To a stirred solution of 2.0 g of fortimicin B (6) 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-concentrated ammonium hydroxide (23.4:1.4:0.1 v/v/v) give 1.05 g of 1,2',6'-tri-N-benzyloxycarbonylfortimicin B: $[\alpha]_D^{25}+16.5°$ (c 1.0, $CH_3OH$); IR 1712 and 1507 cm$^{-1}$; NMR ($CDCl_3$) $\delta 1.03$ ($C_{6'}$—$CH_3$, J=6.0 Hz), 2.32 ($C_4NCH_3$), 3.41 ($OCH_3$).

Anal. Calcd. for $C_{39}H_{50}N_4O_{11}$: C, 62.39; H, 6.71; N, 7.46. Found: C, 62.16; H, 6.76; N, 7.43.

EXAMPLE 6

1,2',6'-Tri-N-benzyloxycarbonyl-4-N-acetylfortimicin B (8)

To a stirred solution of 3.22 g of 1,2',6'-tri-N-benzyloxycarbonylfortimicin B in 225 ml of methanol, cooled in an ice bath, is added 16 ml of acetic anhydride over a 15 minute period. Stirring is continued at 0° C. for 2 hours and then at room temperature for 2 hours. The methanol is evaporated under reduced pressure and residual acetic anhydride and acetic acid are removed by co-distillation with benzene and methanol to leave 3.63 g of 1,2′,6′-tri-N-benzyloxycarbonyl-4-N-acetylfortimicin B: $[\alpha]_D^{25} +58.4°$ (c 1.03, $CH_3OH$); IR 1710, 1620 and 1500 $cm^{-1}$; NMR ($CDCl_3$) $\delta 1.16$ ($C_{6'}$—$CH_3$, J=6.0), 2.07 ($COCH_3$), 2.83 ($C_4$—$NCH_3$), 3.34 ($OCH_3$), 4.81 ($H_{1'}$, J=3.0).

Anal. Calcd. for $C_{41}H_{52}N_4O_{12}$: C, 62.11; H, 6.61; N, 7.07. Found: C, 62.37; H, 6.74; N, 7.00.

EXAMPLE 7

4-N-Acetylfortimicin B Trihydrochloride (9)

A solution of 1.0274 g of tri-N-benzyloxycarbonyl-4-N-acetylfortimicin B in 180 ml of 0.2 N hydrochloric acid in methanol is hydrogenolyzed over 1.2 g of 5% palladium on carbon for 4 hours. The catalyst is removed by filtration through a celite mat. The filtrate is concentrated to dryness under reduced pressure and excess hydrochloric acid is removed by repeated co-distillation with methanol under reduced pressure to give 0.6595 g of 4-N-acetylfortimicin B trihydrochloride: $[\alpha]_D^{25} +87.2°$ (c 1.04, $CH_3OH$); IR (KBr) 1600 and 1485 $cm^{-1}$; NMR ($D_2O$) $\delta 1.80$ ($C_{6'}$—$CH_3$, J=6.9 Hz), 2.62 ($COCH_3$), 3.61 ($C_4$—$NCH_3$), 3.94 ($OCH_3$), 5.77 ($H_{1'}$, J=3.2 Hz); Mass spec. $M^+$. Calcd. 391.2556, Measured 391.2553.

EXAMPLE 8

2-N-Acetylfortimicin B (10)

An aqueous solution of 0.840 g of 4-N-acetylfortimicin B trihydrochloride is passed through a column (1.1×19 cm) of an anion exchange resin, quaternary ammonium sytrene type, e.g., Bio-Rad Laboratories' AG ®2-X8, 50–100 mesh, (hydroxyl form), sufficient to remove the chloride ion. The basic elutes are collected and diluted to 84 ml with water. After standing at room temperature for 20 days the solution is evaporated under reduced pressure to a small volume and chromatographed on a column of a cation exchange resin, carboxylic type, e.g., Bio-Rad Laboratories' Bio-Rex 70, 100–200 mesh, (ammonium form). Elution with a gradient of water to 1 N ammonium hydroxide gives fractions containing only 2′-N-acetylfortimicin B. These fractions are concentrated to dryness under reduced pressure to give 0.390 g of 2′-N-acetylfortimicin B: $[\alpha]_D^{24} +37.6°$ (c 0.95, $CH_3OH$); IR 3350, 1642 and 1557 $cm^{-1}$; NMR ($D_2O$) $\delta 1.51$ ($C_{6'}$—$CH_3$, J=6.0 Hz), 2.42 ($COCH_3$), 2.84 ($C_4$—$NCH_3$), 3.92 ($OCH_3$), 5.66 ($H_{1'}$, J=4.0 Hz). Mass spec (M+H). $C_{17}H_{35}N_4O_6$. Calcd. 391.2557, measured 391.2549.

Anal. Calcd. for $C_{17}H_{34}N_4O_6$ $2H_2O$: C, 47.76; H, 9.19; N, 13.10 Found: C, 47.74; H, 9.28; N, 13.13

EXAMPLE 9

1,6′-Di-N-Dibenzyloxycarbonyl-2′-N-acetylfortimicin B (11)

A stirred solution of 0.290 g of 2′-N-acetylfortimicin B in 4.5 ml of water and 9.0 ml of methanol, cooled to 0° in an ice bath, is treated with 0.388 g of N-(benzyloxycarbonyloxy)succinimide. Stirring is continued at 0° C. for 3 hours and then at room temperature for 22 hours. The solution is concentrated under reduced pressure to an oil which is shaken with a mixture of 100 ml of chloroform and 75 ml of water. The chloroform layer is separated and the aqueous portion is shaken with an additional 100 ml of chloroform. The combined chloroform solutions are washed two times with water and dried over anhydrous magnesium sulfate. Evaporation of the chloroform under reduced pressure leaves 0.480 g of colorless solid. The solid is chromatographed on a column (2.0×43 cm) of silica gel prepared and eluted with a solvent system consisting of chloroform-methanol-concentrated ammonium hydroxide (23.4:1.4:0.1 v/v/v) to give 0.152 g of 1,6′-di-N-benzyloxycarbonyl-2′-N-acetylfortimicin B as a colorless solid: NMR($CDCl_3$) $\delta 0.99$ ($C_{6'}$—$CH_3$, $J_{6',7'}$=7.0 Hz), 192 ($COCH_3$), 2.43 ($NCH_3$), 3.46 ($OCH_3$), 508 ($CbzCH_2$), 7.32 (CbzAr).

EXAMPLE 10

Tri-N-benzyloxycarbonyl-2′-N-acetylfortimicin A (12)

To a stirred solution of 0.150 g of 1,6′-di-N-benzyloxycarbonyl-2′-N-acetylfortimicin B, 0.065 g of N-benzyloxycarbonylglycine and 0.074 g of 1-hydroxybenzotriazole monohydrate in 2.0 ml of tetrahydrofuran is added a solution of 0.069 g of N,N′-dicyclohexylcarbodiimide in 2.0 ml of tetrahydrofuran. Stirring is continued at room temperature for 23 hours. The precipitated N,N′-dicyclohexylurea is removed by filtration. The filtrate is evaporated under reduced pressure to leave 0.299 g of product. The product is chromatographed on a column of silica gel, prepared and eluted with a solvent system consisting of benzene-methanol-95% ethanol-concentrated ammonium hydroxide (23.5:1.4:2.0:0.2 v/v/v/v). Fractions containing the desired product were taken to dryness under reduced pressure leaving 0.178 g of tri-N-benzyloxycarbonyl-2′-N-acetylfortimicin A as a white solid: IR ($CHCl_3$) 3415, 1697, 1633 and 1495 $cm^{-1}$; NMR ($CDCl_3$); $\delta 1.18$ ($C_{6'}CH_3$), 1.94 ($COCH_3$), 3.03 ($C_4$—$NCH_3$), 3.38 ($OCH_3$), 5.08 ($CH_2Cbz$), 7.31 (Cbz-Ar).

EXAMPLE 11

2′-N-Acetylfortimicin A Trihydrochloride (13)

A solution of 0.178 g of tri-N-benzyloxycarbonyl-2′-N-acetylfortimicin A in 30 ml of 0.2 N hydrochloric acid in methanol is hydrogenolyzed for 4 hours under 3 atmospheres of hydrogen in the presence of 0.178 g of 5% palladium on carbon. The catalyst is removed by filtration through a celite mat. The filtrate is concentrated to a small volume and treated with activated carbon, e.g., Darco®G-60, Atlas Chemical Industries, Inc. The carbon is removed by filtration through a celite mat. The filtrate is concentrated to dryness and excess hydrochloric acid is removed by repeated co-distillation with methanol under reduced pressure to give 0.118 g of 2′-N-acetylfortimicin A trihydrochloride

EXAMPLE 12

2′-N-(β-Aminoethyl)fortimicin B (14)

A stirring solution of 2.0 g of 2′-N-glycylfortimicin B in 80 ml of tetrahydrofuran is treated with 1.22 g of lithium aluminum hydride. The stirring reaction mixture is refluxed for 20 hours and then the excess lithium aluminum hydride is consumed by the careful addition of water. The insoluble material is sedimented by centrifugation. The pellet is suspended in 50 ml of water and centrifuged. The combined supernatants are taken to dryness under reduced pressure to give 1.44 g of brown solid. The solid is chromatographed on a column (2.0×40 cm) of cation exchange resin, carboxylic type, e.g., Bio-Rad Laboratories, Bio-Rex 70, 100–200 mesh, (ammonia form), and eluted with a gradient of water to 1 N ammonium hydroxide. Fractions containing the desired product are concentrated to a small volume and lyophilized to give 0.825 g of 2'-N-(β-aminoethyl)fortimicin B.

EXAMPLE 13

1,6'-Di-N-benzyloxycarbonyl-2'-N-[N-benzyloxycarbonyl (β-aminoethyl)]fortimicin B (15)

A stirred solution of 0.824 g of 2'-N-(β-aminoethyl)fortimicin B in 12.4 ml of water and 24.8 ml of methanol cooled to 4° C. in an ice bath, is treated with 1.83 g of N-(benzyloxycarbonyloxy)succinimide. Stirring is continued at 4° C. for 3 hours and then at room temperature for 22 hours. The reaction mixture is concentrated to an oil under reduced pressure and then it is shaken with a mixture of 150 ml of chloroform and 75 ml of water. The chloroform layer is separated and washed with 75 ml of water. The aqueous portions are then washed in series with two 80 ml portions of chloroform. The combined chloroform solution is dried over anhydrous magnesium sulfate and concentrated to dryness under reduced pressure to give 1.584 g of colorless solid. The solid is chromatographed on a column (2.2×65 cm) of silica gel prepared and eluted with a solvent system consisting of benzenemethanol-95% ethanol-concentrated ammonium hydroxide (23.5:1.4:2.0:0.2 v/v/v/v) to give a 0.589 g of 1,2',6'-tri-N-benzyloxycarbonyl-2'-N-[N-benzyloxycarbonyl(β-aminoethyl)]fortimicin B: $[\alpha]_D^{25}-9.5°$ (c 1.0, CH$_3$OH); IR 3440, 1710 and 1510 cm$^{-1}$; NMR (CDCl$_3$) δ0.86 (C$_6'$—CH$_3$, J=7.0 Hz), 2.36 (C$_4$—NCH$_3$); 3.46 (OCH$_3$), 5.11 (Cbz-C$\underline{H}_2$), 7.35 (Cbz-Aromatic)

Anal. Calcd. for C$_{41}$H$_{55}$N$_5$O$_{11}$: C, 62.03; H, 6.98; N, 8.82 Found: C, 61.23; H, 6.98; N, 8.59.

EXAMPLE 14

1,6'-Di-N-benzyloxycarbonyl-4-N-(N-benzyloxycarbonylglycyl)-2'-N-[N-benzyloxycarbonyl(β-aminoethyl)]fortimicin B (16)

A stirred solution of 0.503 g of tri-N-benzyloxycarbonyl-2'-N-[N-benzyloxycarbonyl(β-aminoethyl)]-fortimicin B in 3.4 ml of tetrahydrofuran is treated with 0.223 g of the N-hydroxysuccinimide ester of N-benzyloxycarbonylglycine. After stirring for 20 hours at room temperature, the tetrahydrofuran is evaporated under reduced pressure to leave 0.714 g of colorless solid. The solid is chromatographed on a column (1.5×74 cm) of silica gel eluted with a solvent system consisting of benzene-methanol-95% ethanol-concentrated ammonium hydroxide (23.5:1.4:2.0:0.2 v/v/v/v) to give 0.405 g of 1,6'-di-N-benzyloxycarbonyl-4-N-(N-benzyloxycarbonylglycyl)-2'-N-[N-benzyloxycarbonyl(β-aminoethyl)]fortimicin B: $[\alpha]_D^{24}+32.7°$ (c 1.03, CH$_3$OH); IR 3410, 1705, 1635 and 1500 cm$^{-1}$; NMR (CDCl$_3$) δ1.17 (C$_6$—CH$_3$), 2.91 (C$_4$—NCH$_3$), 3.33 (OCH$_3$), 5.05 (Cbz-C$\underline{H}_2$), 7.29 (Cbz Aromatic).

Anal. Calcd. for C$_{51}$H$_{64}$N$_6$O$_{14}$: C, 62.18; H, 6.55; N, 8.53. Found: C, 62.04; H, 6.56; N, 8.42

EXAMPLE 15

2'-N-(β-Aminoethyl)fortimicin A pentahydrochloride (17)

A solution of 0.426 g of 1,6'-di-N-benzyloxycarbonyl-4-N-(N-benzyloxycarbonylglycyl)-2'-N-[N-benzyloxycarbonyl(β-aminoethyl)]fortimicin B in 70 ml of 0.2 N methanolic hydrochloric acid is hydrogenolyzed over 0.40 g of 5% palladium on carbon for 4 hours. The catalyst, collected by filtration through a celite mat, is washed with several small portions of methanol. The filtrate is evaporated to dryness under reduced pressure. Excess hydrochloric acid is removed by repeated codistillation with methanol under reduced pressure to give 0.268 g of 2'-N-(β-aminoethyl)fortimicin A pentahydrochloride: $[\alpha]_D^{24}+67.7°$ (c 1.0, CH$_3$OH); IR 3420, 2940, 1643, 1600 and 1485 cm$^{-1}$; NMR (D$_2$O) δ2.78 (C$_6'$—CH$_3$, J=7.0 Hz), 3.57 (C$_4$—N-CH$_3$), 3.93 (OCH$_3$), 5.88 (H$_{1'}$, J=4.0 Hz). Mass spec. M$^+$ Calcd. 448.3009, Measured 448.2291.

The compounds of this invention are active as systemic antibiotics when injected by parenteral routes of administration, i.e., by the intramuscular, intravenous, intraparitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 1 to 100 mg/kg of body weight daily are administered to a mammalian patient suffering from an infection caused by susceptable organism.

The antibacterial activity of the compounds of this invention is initially determined by a two-fold dilution test using Meuller-Hinton agar, 10 ml per Petri plate. The inoculum of approximately 1×10$^5$ of the indicated test organism is delivered by the Steer's replicator. The test is incubated at 37° C. for 24 hours.
TABLE I
Reaction Scheme For Preparation Of Representative Compounds Of This Invention
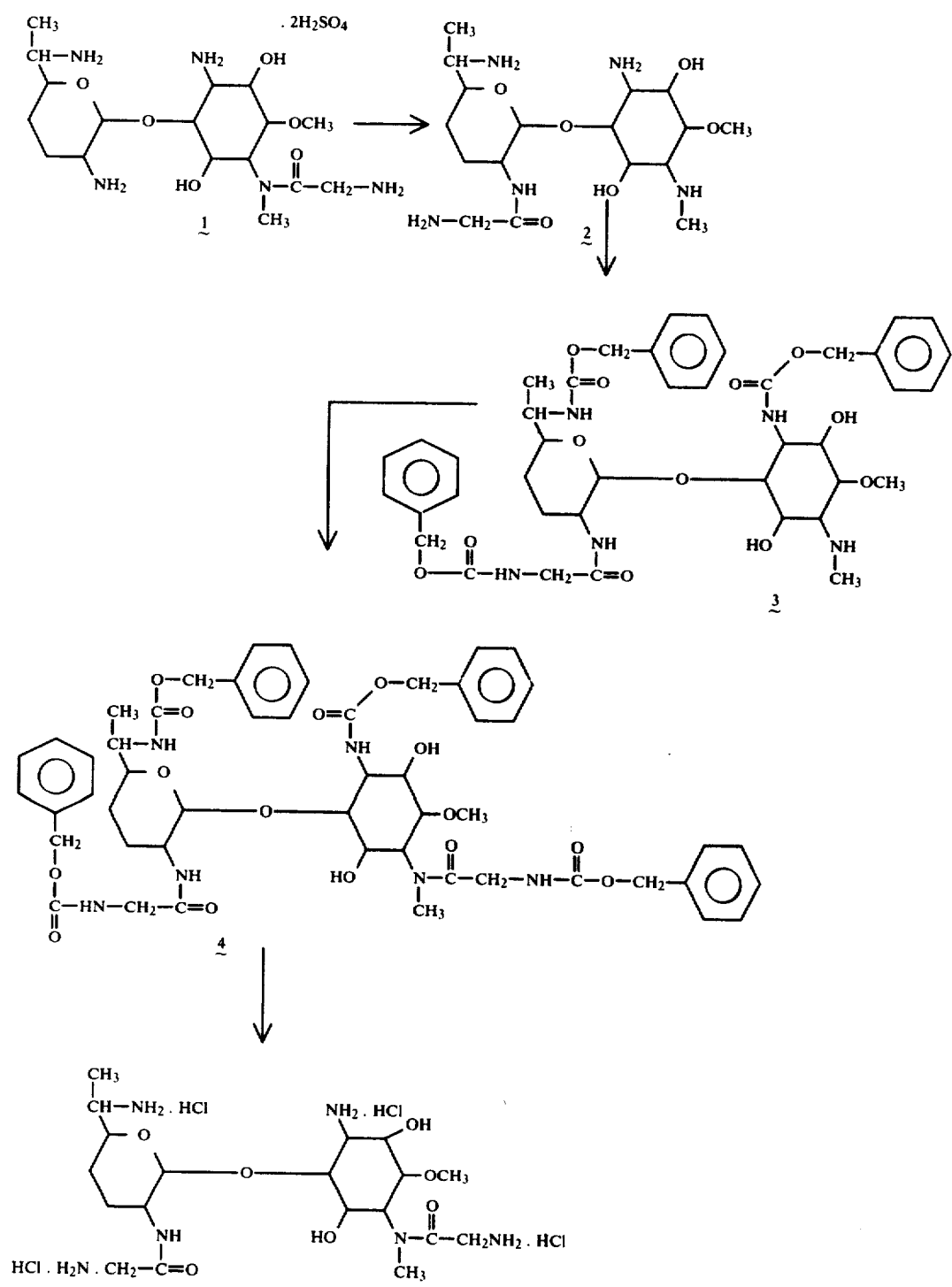

TABLE I-continued
Reaction Scheme For Preparation Of Representative
Compounds Of This Invention
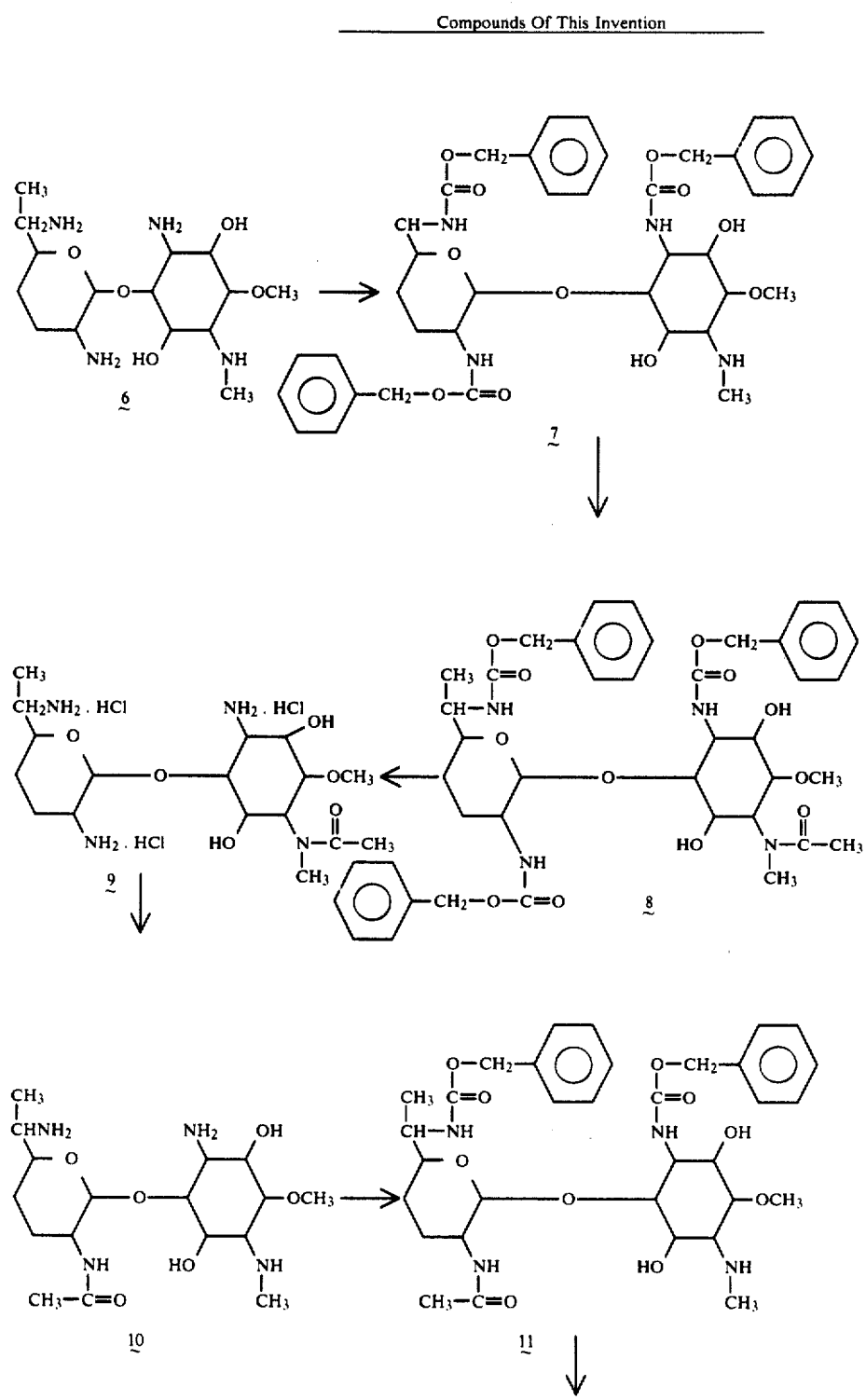

TABLE I-continued
Reaction Scheme For Preparation Of Representative Compounds Of This Invention
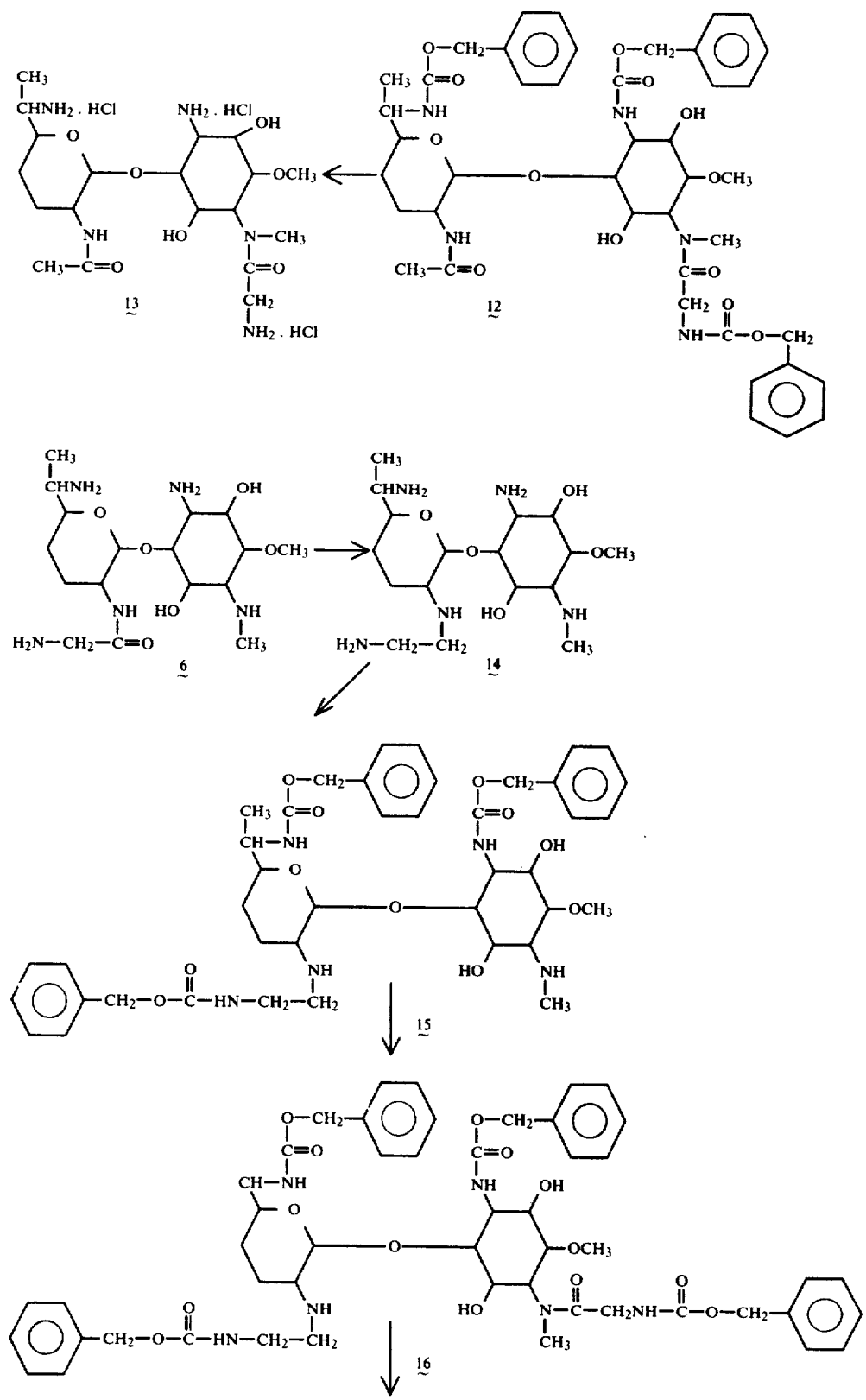

TABLE I-continued
Reaction Scheme For Preparation Of Representative Compounds Of This Invention

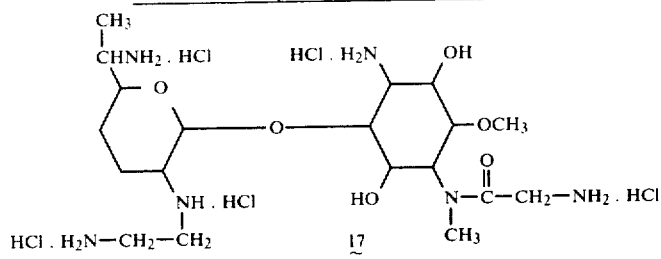

We claim:
1. A fortimicin B derivative selected from the group consisting of 2′N-acyl and alkyl fortimicin B and fortimicin B derivatives, 4,2′-N,N′-diacyl and dialkyl derivatives, 4-N-acyl-2′-N-alkyl and 4-N-alkyl-2′-N-acyl fortimicin B derivatives represented by the formula:

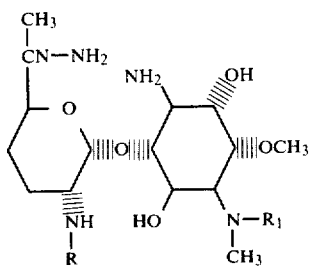

wherein: R is acyl, aminoacyl, N-monoloweralkylaminoacyl, N,N-diloweralkylaminoacyl, hydroxy-substituted aminoacyl, hydroxyacyl, an amino acid residue selected from the group consisting of L, D or DL glycyl, alanyl, sarcosyl, tyrosyl, phenylalanyl, methionyl, seryl, lysyl, asparginyl, isoleucyl, leucyl, histidyl, threonyl, aspartyl, asparaginyl, valyl, prolyl, glutaminyl, tryptophanyl, and glutamyl, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, or N,N-diloweralkylaminohydroxyloweralkyl; and $R_1$ is acyl, aminoacyl, N-monoloweralkylaminoacyl, N,N-diloweralkylaminoacyl, hydroxy-substituted aminoacyl, hydroxyacyl an amino acid residue, loweralkyl, aminoloweralkyl, hydroxyloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl or hydrogen; with the limitation that $R_1$ cannot be hydrogen when R is glycyl and the pharmaceutically acceptable salts thereof, and wherein acyl is

$R_4$ being loweralkyl.
2. A compound of claim 1 wherein $R_1$ is hydrogen.
3. A compound of claim 2: 2′-N-glycylfortimicin B or a pharmaceutically acceptable salt thereof.
4. A compound of claim 2: 2′-N-(β-aminoethyl)-fortimicin B or a pharmaceutically acceptable salt thereof.
5. A compound of claim 1 wherein both R and $R_1$ are an amino acid residue.
6. A compound of claim 5: 2′-N-glycylfortimicin A or a pharmaceutically acceptable salt thereof.
7. A compound of claim 1 wherein R is aminoloweralkyl.
8. A compound of claim 1 wherein R is an amino acid residue.
9. A compound of claim 1 wherein R is acyl.
10. A compound of claim 1 wherein R is loweralkyl.
11. 2′-N-glycylfortimicin B trihydrochloride.
12. 2′-N-glycylfortimicin A.
13. 2′-N-glycylfortimicin A trihydrochloride.
14. 2′-N-acetylfortimicin B.
15. 2′-N-acetylfortimicin B trihydrochloride.
16. 2′-N-acetylfortimicin A.
17. 2′-N-acetylfortimicin A trihydrochloride.
18. 2′-N-(β-aminoethyl)fortimicin B.
19. 2′-N-(β-aminoethyl)fortimicin A.
20. 2′-N-(β-aminoethyl)fortimicin A pentahydrochloride.
21. A pharmaceutical composition comprising a compound of claim 1 and a pharmaceutically acceptable carrier or diluent.

* * * * *